United States Patent
Zaspel et al.

(10) Patent No.: US 11,890,374 B2
(45) Date of Patent: *Feb. 6, 2024

(54) USE OF AN ORAL BOLUS IN THE DRYING-OFF OF DAIRY CATTLE

(71) Applicant: Boehringer Ingelheim Vetmedica GmbH, Ingelheim am Rhein (DE)

(72) Inventors: Daniel Zaspel, Birkenwerder (DE); Juergen Bubeck, Munster-Sarmsheim (DE); Holger Enderle, Windesheim (DE); Laurent Goby, Frankfurt am Main (DE); Leif Hoejvang-Nielsen, Fredensborg (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/189,317

(22) Filed: Mar. 2, 2021

(65) Prior Publication Data

US 2021/0177747 A1 Jun. 17, 2021

Related U.S. Application Data

(63) Continuation of application No. 16/416,428, filed on May 20, 2019, now Pat. No. 10,966,921.

(30) Foreign Application Priority Data

May 23, 2018 (EP) .................................. 18173742

(51) Int. Cl.
| | | |
|---|---|---|
| *A61K 9/00* | (2006.01) | |
| *A23K 20/20* | (2016.01) | |
| *A23K 20/24* | (2016.01) | |
| *A23K 50/10* | (2016.01) | |
| *A61K 33/02* | (2006.01) | |
| *A61K 33/04* | (2006.01) | |
| *A61K 33/06* | (2006.01) | |
| *A61K 33/14* | (2006.01) | |
| *A61K 33/20* | (2006.01) | |
| *A61P 43/00* | (2006.01) | |

(52) U.S. Cl.
CPC ............ *A61K 9/0053* (2013.01); *A23K 20/20* (2016.05); *A23K 20/24* (2016.05); *A23K 50/10* (2016.05); *A61K 33/02* (2013.01); *A61K 33/04* (2013.01); *A61K 33/06* (2013.01); *A61K 33/14* (2013.01); *A61P 43/00* (2018.01); *A61K 33/20* (2013.01)

(58) Field of Classification Search
None
See application file for complete search history.

(56) References Cited

U.S. PATENT DOCUMENTS

| | | | |
|---|---|---|---|
| 5,360,823 A | 11/1994 | Griffel, Jr. et al. | |
| 5,686,125 A | 11/1997 | Mueller | |
| 9,497,981 B2 | 11/2016 | Fahrenholz et al. | |
| 10,966,921 B2 * | 4/2021 | Zaspel | A61K 33/02 |
| 11,723,919 B2 | 8/2023 | Zanzalari et al. | |
| 2002/0150633 A1 | 10/2002 | Danzer et al. | |
| 2002/0176883 A1 | 11/2002 | Block et al. | |
| 2018/0206528 A1 | 7/2018 | Costigan et al. | |
| 2021/0023145 A1 * | 1/2021 | Wood | A23L 33/135 |
| 2021/0161930 A1 | 6/2021 | Reiche | |

FOREIGN PATENT DOCUMENTS

| | | |
|---|---|---|
| CN | 105029016 A | 11/2015 |
| EP | 0943246 A1 | 9/1999 |

OTHER PUBLICATIONS

English translation for CN 105029016 A (Wei et al). (Year: 2015).*
Tucker, C. B., S. J. Lacy-Hulbert, and J. R. Webster. "Effect of milking frequency and feeding level before and after dry off on dairy cattle behavior and udder characteristics." Journal of dairy science 92.7 (2009): 3194-3203.
Rérat, M., and P. Schlegel. "Effect of dietary potassium and anionic salts on acid-base and mineral status in periparturient cows." Journal of animal physiology and animal nutrition 98.3 (2014): 458-466.
Stokes, Sandra R. "Anionic Salt Programs for Close-Up Dry Cows." Texas Farmer Collection (1998).
Oetzel, G. R., and B. E. Miller. "Effect of oral calcium bolus supplementation on early-lactation health and milk yield in commercial dairy herds." Journal of dairy science 95.12 (2012): 7051-7065.
Rajala-Schultz, P. J., et al. "Effect of milk cessation method at dry-off on behavioral activity of dairy cows." Journal of dairy science 101.4 (2018): 3261-3270.
Britt, J. S., et al. "Efficiency of converting nutrient dry matter to milk in Holstein herds." Journal of Dairy Science 86.11 (2003): 3796-3801.

(Continued)

*Primary Examiner* — Sin J Lee

(57) ABSTRACT

Described herein is an oral bolus for drying-off cattle, preferably dairy cattle, as well as methods of improving/facilitating the drying-off of cattle, reducing the milk production in pregnant and/or lactating cattle, decreasing milk accumulation in the udder of cattle, increasing the daily lying time of cattle, inducing a mild and temporary metabolic acidosis in cattle, reducing the dry matter intake (DMI) in cattle and/or reducing urine pH in cattle, preferably dairy cattle, including administering to such cattle at least one oral bolus, preferably on the last milking day and/or before dry-off.

13 Claims, 6 Drawing Sheets

(56) References Cited

OTHER PUBLICATIONS

Razzaghi, A., et al. "Effect of dietary cation-anion difference during prepartum and postpartum periods on performance, blood and urine minerals status of holstein dairy cow." Asian-Australasian journal of animal sciences 25.4 (2012): 486.
Sampson, J. D., et al. "Effects of calcium chloride and calcium sulfate in an oral bolus given as a supplement to postpartum dairy cows." Veterinary therapeutics: research in applied veterinary medicine 10.3 (2009): 131-139.
Jin Rui, "Nutritional Regulation of Periparturient Anionic Diets for Dairy Cows," Jilin Agriculture, No. 07, 2012, pp. 182-183.
Bovikalc Dry, Drugs.com, 2022, Animalytix LLC, Updated: Jun. 30, 2022.
"Animate," web page downloaded from https://www.pahc.com/animate/home/ on Oct. 27, 2023, 11 pages.

\* cited by examiner

USE OF AN ORAL BOLUS IN THE DRYING-OFF OF DAIRY CATTLE

CROSS REFERENCE TO RELATED APPLICATIONS

This application is a continuation of U.S. patent application Ser. No. 16/416,428, filed May 20, 2019, which claims priority from European Patent Application No. 18173742.0, filed May 23, 2018, the disclosures of which are incorporated herein by reference in their entireties.

FIELD OF THE INVENTION

The invention relates to the field of medicine, particularly veterinary medicine. In particular, the invention relates to the use of oral, preferably anionic salt comprising boluses or acidogenic boluses in the drying-off of cattle, preferably dairy cattle.

BACKGROUND OF THE INVENTION

Drying-off cows has been widely recognized as a critical period of the production cycle of cows. It has been suggested, that with increasing milk yields over the last decades, the transition from lactating to dry has progressively become more challenging for cows in terms of animal health and welfare. From an animal health perspective, cessation of milking has been associated with increased risk of new intra-mammary infections that may persist onto the following lactation with detrimental consequences on milk production. One of the factors contributing to this increased risk is the continued milk production in the mammary gland in the immediate period following drying-off: the milk is accumulated in the udder and the increased udder pressure may cause milk leakage (ML) from the teats. Milk leakage may allow microorganisms to colonize the udder coinciding with a moment of impaired natural protective activity in the mammary gland due to the involution process. In addition to ML, the increased intra-mammary pressure after cessation of milking has been suggested to potentially cause discomfort to cows, which in turn may alter lying behavior.

The current state of the art is progressive or brutal cessation of milking combined with change in feeding diet. Drugs like cabergoline may be used. However, cabergoline is a synthetic ergot derivative, which is a potent dopamine receptor agonist on D2 receptors. It acts on dopamine receptors of prolactin producing cells in the pituitary gland suppressing the prolactin production and leading to the inhibition of prolactin secretion dependent process.

Consequently, cabergoline administration induces a reduction of milk production leading to a reduction in udder engorgement and intramammary pressure. Cabergoline is registered in some countries for use in dairy cows as an aid in the abrupt drying-off by reducing milk production to reduce milk leakage at drying off, reduce the risk of new intramammary infections during the dry period and reduce discomfort. However, the marketing authorizations for cabergoline in the EU were suspended in 2016 due to suspected serious adverse effects.

Rérat M and Schlegel P (Journal of Animal Physiology and Animal Nutrition 2013, 98(3): 458-466) describe the effect of dietary potassium and anionic salts on acid base and mineral status in periparturient cows.

Stokes S R (http://oaktrust.library.tamu.edu/bitstream/handle/1969.1/86766/pdf_1016.pdf?sequence=1) describes anionic salt programs for close-up dry cows.

US 2002/0150633 describes dry dairy cow supplement.

EP 0 943 246 describes a complete fodder for the feeding of cows during the dry period.

U.S. Pat. No. 5,360,823 describes an anionic salt formulation for milk fever prevention in dairy cows and treatment method.

Oetzel G R and Miller B E (Journal of Dairy Science 2012, 95(12): 7051-7065) describe the effect of oral calcium bolus supplementation on early-lactation health and milk yield in commercial herds.

There is an urgent need for the improvement/facilitation of drying-off of cattle which overcomes the problems of the prior art.

SUMMARY OF THE INVENTION

The present invention concerns the use of an oral bolus for drying-off cattle, preferably dairy cattle.

A corresponding method of drying-off cattle, preferably dairy cattle comprising administering an oral bolus, a corresponding oral bolus for use in a method of drying-off cattle, preferably dairy cattle, as well as the corresponding use of an oral bolus for the preparation of a medicament for drying-off cattle, preferably dairy cattle, are also intended to be comprised by the present invention.

The present invention also concerns a method of improving/facilitating the drying-off of cattle, preferably dairy cattle, comprising administering to such cattle at least one oral bolus, preferably on the last milking day and/or preferably before dry-off.

A corresponding use of at least one oral bolus for improving/facilitating the drying-off of cattle, preferably dairy cattle, wherein such at least one oral bolus is administered to such cattle preferably on the last milking day and/or preferably before dry-off, a corresponding at least one oral bolus for use in a method of improving/facilitating the drying-off of cattle, preferably dairy cattle, wherein such at least one oral bolus is administered to such cattle preferably on the last milking day and/or preferably before dry-off as well as the corresponding use of at least one oral bolus for the preparation of a medicament for improving/facilitating the drying-off of cattle, preferably dairy cattle, wherein such at least one oral bolus is administered to such cattle preferably on the last milking day and/or preferably before dry-off, are also intended to be comprised by the present invention.

The present invention also concerns a method of reducing the milk production in pregnant and/or lactating cattle, preferably pregnant and/or lactating dairy cattle, comprising administering to such cattle at least one oral bolus, preferably on the last milking day and/or preferably before dry-off.

A corresponding use of at least one oral bolus for reducing the milk production in pregnant and/or lactating cattle, preferably pregnant and/or lactating dairy cattle, wherein such at least one oral bolus is administered to such cattle preferably on the last milking day and/or preferably before dry-off, a corresponding at least one oral bolus for use in a method of reducing the milk production in pregnant and/or lactating cattle, preferably pregnant and/or lactating dairy cattle, wherein such at least one oral bolus is administered to such cattle preferably on the last milking day and/or preferably before dry-off as well as the corresponding use of at least one oral bolus for the preparation of a medicament for reducing the milk production in pregnant and/or lactating cattle, preferably pregnant and/or lactating dairy cattle, wherein such at least one oral bolus is administered to such cattle preferably on the last milking day and/or preferably before dry-off, are also intended to be comprised by the present invention.

The present invention also concerns a method of decreasing milk accumulation in the udder of cattle, preferably dairy cattle, comprising administering to such cattle at least one oral bolus, preferably on the last milking day and/or preferably before dry-off.

A corresponding use of at least one oral bolus for decreasing milk accumulation in the udder of cattle, preferably dairy cattle, wherein such at least one oral bolus is administered to such cattle preferably on the last milking day and/or preferably before dry-off, a corresponding at least one oral bolus for use in a method of decreasing milk accumulation in the udder of cattle, preferably dairy cattle, wherein such at least one oral bolus is administered to such cattle preferably on the last milking day and/or preferably before dry-off as well as the corresponding use of at least one oral bolus for the preparation of a medicament for decreasing milk accumulation in the udder of cattle, preferably dairy cattle, wherein such at least one oral bolus is administered to such cattle preferably on the last milking day and/or preferably before dry-off, are also intended to be comprised by the present invention.

The present invention also concerns a method of increasing the daily lying time of cattle, preferably dairy cattle, comprising administering to such cattle at least one oral bolus, preferably on the last milking day and/or preferably before dry-off.

A corresponding use of at least one oral bolus for increasing the daily lying time of cattle, preferably dairy cattle, wherein such at least one oral bolus is administered to such cattle preferably on the last milking day and/or preferably before dry-off, a corresponding at least one oral bolus for use in a method of increasing the daily lying time of cattle, preferably dairy cattle, wherein such at least one oral bolus is administered to such cattle preferably on the last milking day and/or preferably before dry-off as well as the corresponding use of at least one oral bolus for the preparation of a medicament for increasing the daily lying time of cattle, preferably dairy cattle, wherein such at least one oral bolus is administered to such cattle preferably on the last milking day and/or preferably before dry-off, are also intended to be comprised by the present invention.

The present invention also concerns a method of inducing a mild and temporary metabolic acidosis in cattle, preferably dairy cattle, at dry-off, comprising administering to such cattle at least one oral bolus, preferably on the last milking day and/or preferably before dry-off.

A corresponding use of at least one oral bolus for inducing a mild and temporary metabolic acidosis in cattle, preferably dairy cattle, wherein such at least one oral bolus is administered to such cattle preferably on the last milking day and/or preferably before dry-off, a corresponding at least one oral bolus for use in a method of inducing a mild and temporary metabolic acidosis in cattle, preferably dairy cattle, wherein such at least one oral bolus is administered to such cattle preferably on the last milking day and/or preferably before dry-off as well as the corresponding use of at least one oral bolus for the preparation of a medicament for inducing a mild and temporary metabolic acidosis in cattle, preferably dairy cattle, wherein such at least one oral bolus is administered to such cattle preferably on the last milking day and/or preferably before dry-off, are also intended to be comprised by the present invention.

The present invention also concerns a method of reducing the dry matter intake (DMI) in cattle, preferably dairy cattle, comprising administering to such cattle at least one oral bolus, preferably on the last milking day and/or preferably before dry-off.

A corresponding use of at least one oral bolus for reducing the dry matter intake (DMI) in cattle, preferably dairy cattle, wherein such at least one oral bolus is administered to such cattle preferably on the last milking day and/or preferably before dry-off, a corresponding at least one oral bolus for use in a method of reducing the dry matter intake (DMI) in cattle, preferably dairy cattle, wherein such at least one oral bolus is administered to such cattle preferably on the last milking day and/or preferably before dry-off as well as the corresponding use of at least one oral bolus for the preparation of a medicament for reducing the dry matter intake (DMI) in cattle, preferably dairy cattle, wherein such at least one oral bolus is administered to such cattle preferably on the last milking day and/or preferably before dry-off, are also intended to be comprised by the present invention.

The present invention also concerns a method of reducing urine pH in cattle, preferably dairy cattle, comprising administering to such cattle at least one oral bolus, preferably on the last milking day and/or preferably before dry-off.

A corresponding use of at least one oral bolus for reducing urine pH in cattle, preferably dairy cattle, wherein such at least one oral bolus is administered to such cattle preferably on the last milking day and/or preferably before dry-off, a corresponding at least one oral bolus for use in a method of reducing urine pH in cattle in cattle, preferably dairy cattle, wherein such at least one oral bolus is administered to such cattle preferably on the last milking day and/or preferably before dry-off as well as the corresponding use of at least one oral bolus for the preparation of a medicament for reducing urine pH in cattle in cattle, preferably dairy cattle, wherein such at least one oral bolus is administered to such cattle preferably on the last milking day and/or preferably before dry-off, are also intended to be comprised by the present invention.

The advantages according to the present invention are one or more of the following
- reduction of milk production in pregnant and/or lactating cattle, preferably for at least 48 h following bolus administration;
- decreased milk accumulation in the udder and thereby reduced udder pressure, preferably during the days after dry-off and when bolus administration occurred 8 h to 12 h before dry-off;
- increase in the daily lying time, preferably on the days after dry-off;
- induction of a mild and temporary metabolic acidosis at dry-off;
- reduction of dry matter intake (DMI), preferably during the days after dry-off; and/or
- reduction of urine pH, after bolus administration.

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

In the course of the present invention "bolus" is defined as follows: a solid dosage form providing preferably at least 5 g of a substance/material or a combination of substances/materials administered for prophylactic or therapeutic purposes.

In the course of the present invention "drying-off" is defined as follows: cessation of milking of a lactating cow.

In the course of the present invention "improving/facilitating the drying-off" is defined as follows: faster reduction of milk production.

In one aspect the present invention concerns the uses as herein described and claimed or the methods as herein described and claimed, wherein the administration of the oral bolus, preferably on the last milking day and/or preferably before dry-off, leads to one or more of the following effects:
(a) reduction of milk production in pregnant and/or lactating cattle, preferably for at least 48 h following bolus administration; and/or
(b) decrease of milk accumulation in the udder and thereby reduced udder pressure, preferably during the days after dry-off and when bolus administration occurred 8 h to 12 h before dry-off; and/or
(c) increase of the daily lying time, preferably on the day after dry-off; and/or
(d) induction of a mild and temporary metabolic acidosis at dry-off; and/or
(e) reduction of dry matter intake (DMI), preferably during the days after dry-off; and/or
(f) reduction of urine pH following bolus administration In another aspect the present invention concerns the uses as herein described and claimed or the methods as herein described and claimed, wherein the oral bolus is an oral anionic salt comprising bolus or acidogenic bolus.

In the course of the present invention "anionic salt comprising bolus or acidogenic bolus" is defined as follows: bolus containing as active ingredient(s) acidifying agents as defined herein.

In another aspect the present invention concerns the uses as herein described and claimed or the methods as herein described and claimed, wherein the oral anionic salt comprising bolus or acidogenic bolus comprises one or more acidifying agents as feed additives/feed supplements.

In the course of the present invention "acidifying agents" is defined as follows: agents, which—when administered orally—change the pH of the cow's blood and/or urine in a negative direction compared to the normal physiological values of approximately pH 7.44 for blood and pH 8.30 for urine.

In another aspect the present invention concerns the uses as herein described and claimed or the methods as herein described and claimed, wherein the one or more acidifying agents are selected from the group consisting of: ammonium chloride, calcium chloride and/or calcium sulfate.

In another aspect the present invention concerns the uses as herein described and claimed or the methods as herein described and claimed, wherein the one or more acidifying agents are ammonium chloride and calcium chloride and calcium sulfate, more preferably 10.4% (w/w) ammonium chloride and 51.9% (w/w) calcium chloride and 20.1% (w/w) calcium sulfate.

In another aspect the present invention concerns the uses as herein described and claimed or the methods as herein described and claimed, wherein such cattle are pregnant and/or lactating cows, preferably pregnant and/or lactating Holstein cows.

In another aspect the present invention concerns the uses as herein described and claimed or the methods as herein described and claimed, wherein the oral bolus is administered once, twice, three-times, four-times or more times, preferably on the last milking day and/or before dry-off.

In another aspect the present invention concerns the uses as herein described and claimed or the methods as herein described and claimed, wherein the oral bolus is administered twice, more preferably on the last milking day and/or before dry-off, more preferably, about 12 h to 8 h before last milking preceding the dry-off.

In yet another aspect the present invention concerns a calcium containing preparation in solid bolus form, comprising one or more acidifying agents, preferably selected from the group consisting of: ammonium chloride, calcium chloride and/or calcium sulfate, more preferably ammonium chloride and calcium chloride and calcium sulfate, even more preferably 5% (w/w) to 15% (w/w) ammonium chloride and 40% (w/w) to 60% (w/w) calcium chloride and 15% (w/w) to 25% (w/w) calcium sulfate, most preferably 10.4% (w/w) ammonium chloride and 51.9% (w/w) calcium chloride and 20.1% (w/w) calcium sulfate.

EXAMPLES

Figure 1:
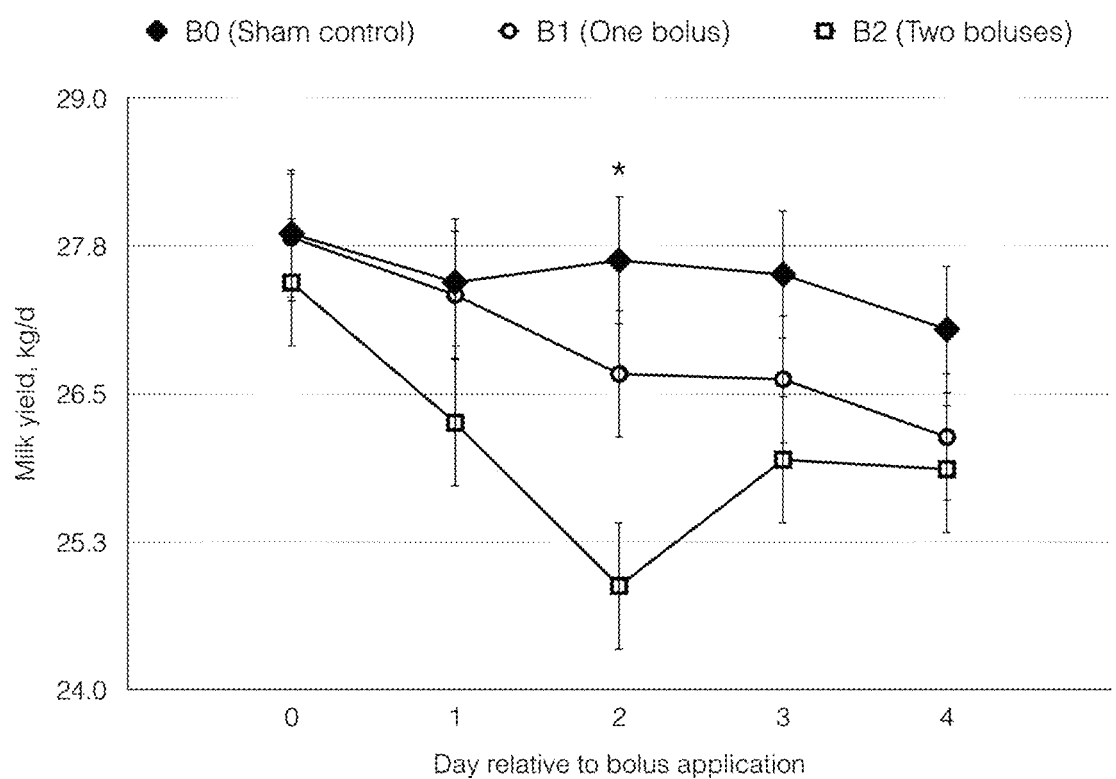
FIG. 1: shows milk production in pregnant and lactating cows receiving no treatment (B0); cows receiving one acidogenic bolus after the last milking of day 0 (B1); and cows receiving two acidogenic boluses after the last milking of day 0 (B2). Error bars depict SEM at each time point. Asterisk depicts a difference (P<0.05) between Control and Bolus.

The following examples serve to further illustrate the present invention; but the same should not be construed as a limitation of the scope of the invention disclosed herein.

Example 1

The objective of this experiment was to determine the effect of the administration of different numbers of acidogenic boluses to lactating cows on milk yield. In order to assess the effects on milk yield, this experiment was performed in pregnant and lactating cows during the week before the scheduled date of dry-off.

Animals, Experimental Design and Measurements

First, 84 lactating and pregnant (28.1±6.17 kg/d of milk yield and 222±3.2 d pregnant) Holstein cows were blocked by parity (29 primiparous and 55 multiparous) and randomly allocated (using the random generator function of Excel, Microsoft Corp., Redmond, WA) to one of the following 3 treatments: 1 bolus applied 5 d before dry-off (B1); 2 boluses applied 5 min apart 5 d before dry-off (B2); and a sham bolus applied 5 d before dry-off (B0). The mineral composition of the oral bolus each weighing 196 g (Bovikalc Dry, Boehringer Ingelheim Vetmedica GmbH, Germany) was: $NH_4Cl$ (10.4%), calcium chloride ($CaCl_2$, 51.9%) and calcium sulfate ($CaSO_4$, 20.1%). Each bolus provided approximately 20 g of ammonium chloride.

Cows were enrolled at the end of their lactation (341±32.2 DIM) and daily milk production was recorded for 15 d prior to dry-off using electronic milk meters (Westfalia Surge Metatron Milk Meter; GEA Farm Technologies, Barcelona, Spain). The inclusion criteria for animal enrollment were a good general health based on physical inspection, a daily milk yield >15 kg, no signs of clinical mastitis, and four functional quarters.

All enrolled cows were kept in a barn equipped with free-stalls, had ad libitum access to water, were fed twice daily a lactation TMR following NRC (2001) recommendations, and were milked 3 times daily.

Statistical Analyses

The potential effect of bolus administration on daily milk production was analyzed with a mixed-effects model with repeated measures using the PROC MIXED procedure of SAS (version 9.2, SAS Institute Inc., Cary, NC). The fixed part of the model accounted for the effect of treatment, day relative to treatment application (5 d before dry-off) and their 2-way interaction, and the random part accounted for the effect of block (parity) and cow within treatment. Time entered the model as repeated measure using a first order autoregressive variance-covariance matrix as it yielded the lowest Bayesian information criterion values. Average milk production between -15 and -6 d relative to dry-off was used as a covariate. Because treatment was applied at the animal level, the experimental unit was the animal. One cow from the B0 treatment was removed from the study because of illness.

Milk Production

Milk production was affected by an interaction (P<0.01) between treatment and days elapsed since bolus application with the greatest decrease in milk production attained 2 d after bolus administration in B2 (FIG. 1). Overall, these results demonstrate that oral administration of two acidogenic boluses to pregnant and lactating cows reduces milk production >2 kg/d the second day after application.

Example 2

The objective of this experiment was to corroborate the effects of the administration of two acidogenic boluses on milk yield and to determine the potential impact on dry matter intake (DMI) and urine pH.

Animals and Experimental Design

Sixteen (8 primiparous and 8 multiparous) lactating and pregnant (154±19.4 d pregnant) Holstein cows (273±56.4 DIM, and 31.7±5.59 kg/d of milk yield) were enrolled in a cross-over experiment consisting of 2 periods of 9 d each and 2 treatments consisting of no supplementation (Control) or supplementation with $NH_4Cl$ combined with $CaCl_2$ and $CaSO_4$ via two oral boluses (Bovikalc Dry, Boehringer Ingelheim Vetmedica GmbH, Germany) administered 5 min apart (Bolus) at day zero of each experimental period.

Before initiating the treatment phase, milk yield and feed intake of all cows were monitored on a daily basis for 9 d as a base-line reference period. Then, cows were randomly allocated to either Bolus or Control. After 9 d, treatment groups were reversed following a cross-over design.

Cows were kept in a barn equipped with free-stalls, milked twice daily, and had ad libitum access to water and feed in the form of a TMR balanced according NRC (2001) recommendations.

Measurements

Daily individual feed intake was monitored throughout the study using electronic feed bins (MooFeeder, MooSystems, Spain) that recorded time of the day and amount of feed consumed at every visit as described in Bach et al. (2017). Individual milk production at every milking was measured using electronic milk meters (AfiMilk, Afikim Ltd., Israel). Urine samples were collected at 0, 8, 24, and 48 h relative to bolus application using from all cows by manual stimulation and urine pH immediately measured using a portable pH-meter (CRISON pH25, CRISON Instruments SA, Spain) that was calibrated before sampling with pH 4.0 and 7.0 buffer solutions.

Statistical Analyses

Daily milk production, feed intake, and urine pH were analyzed using a mixed-effects model that accounted for the fixed effect of treatment, day of study, and their 2-way interaction, plus the random effect of cow, period, and sequence in the cross over as random effects. Time entered the model as repeated measure using a first order autoregressive variance-covariance matrix as it yielded the lowest Bayesian information criterion values. Daily milk production and feed intake during the first 9 d of study (base-line) were averaged and entered the statistical model as a covariate. All analyses were performed with SAS. Because treatment was applied at the animal level, the experimental unit was the animal.

Urine pH

Figure 2:
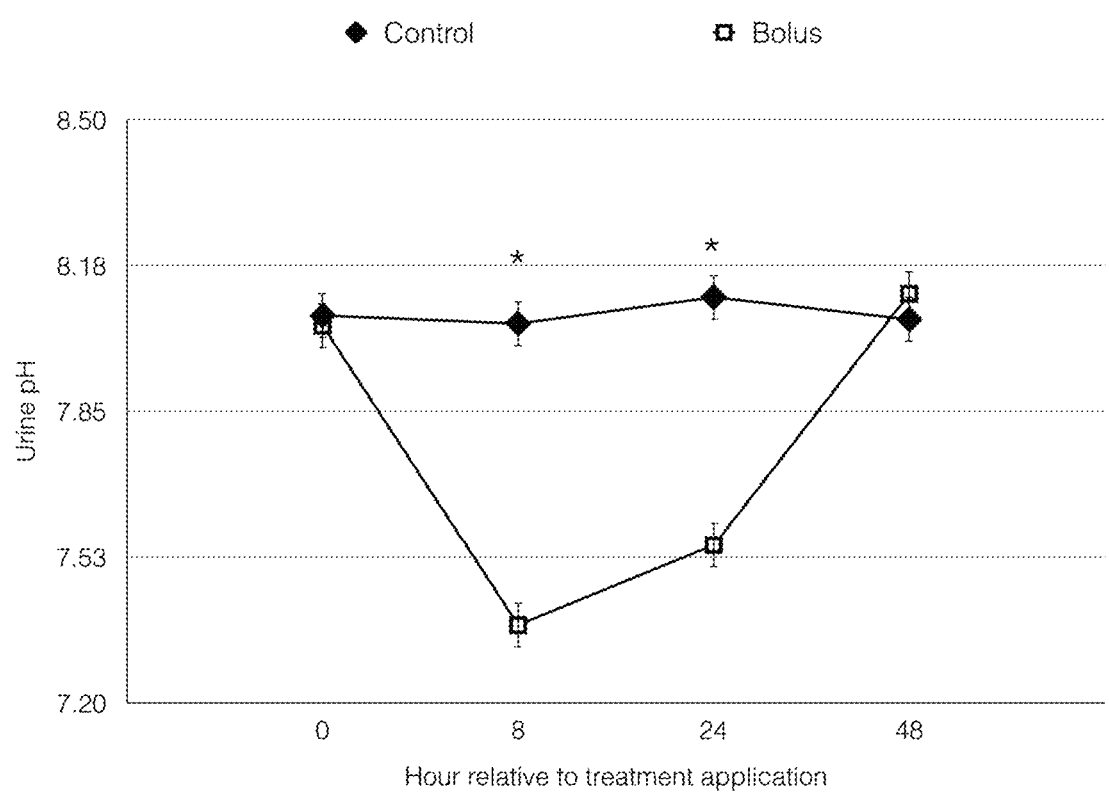
FIG. 2: shows urine pH as affected by bolus application [closed diamonds correspond to cows receiving no treatment (Control); open squares correspond to cows that received oral boluses (Bolus)]. Error bars depict SEM at each time point. Asterisk depicts difference (P<0.05) between Control and Bolus.

Urine pH of Bolus cows declined (P<0.05) after bolus application from 8.04±0.05 at time zero to 7.37±0.05 and 7.55±0.05 at 8 and 24 h post-treatment, respectively, and then returned to similar values as those of time zero. No differences in urine pH were observed in Control cows among sampling times, and was ~8.07 throughout the sampling period (FIG. 2).

Animal Performance

Figure 3:
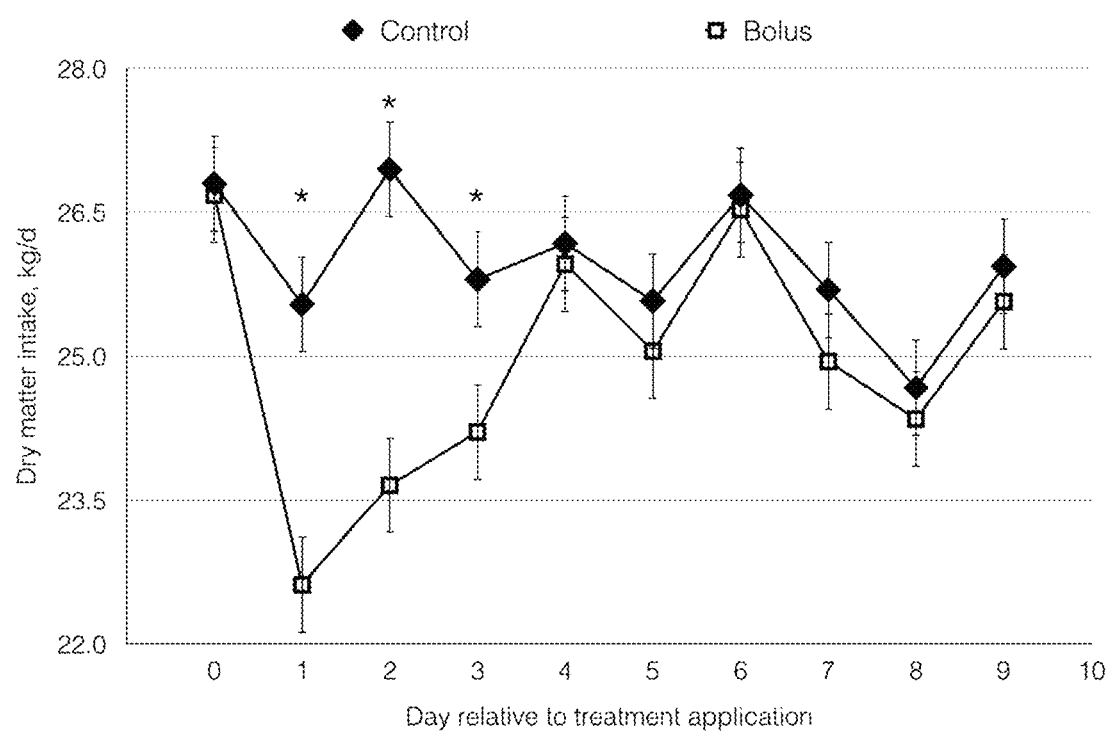
FIG. 3: shows dry matter intake as affected by bolus application [closed diamonds correspond to cows receiving no treatment (Control); open squares correspond to cows that received oral boluses (Bolus)]. Error bars depict SEM at each time point. Asterisk depicts difference (P<0.05) between Control and Bolus.

Dry matter intake (DMI) was reduced (P<0.01) in Bolus cows (24.8±0.50 kg/d) compared with Control cows (25.9±0.50 kg/d). There was an interaction (P<0.05) between treatment and day, with decreases in DMI during the first 3 d following treatment application (FIG. 3).

Figure 4:
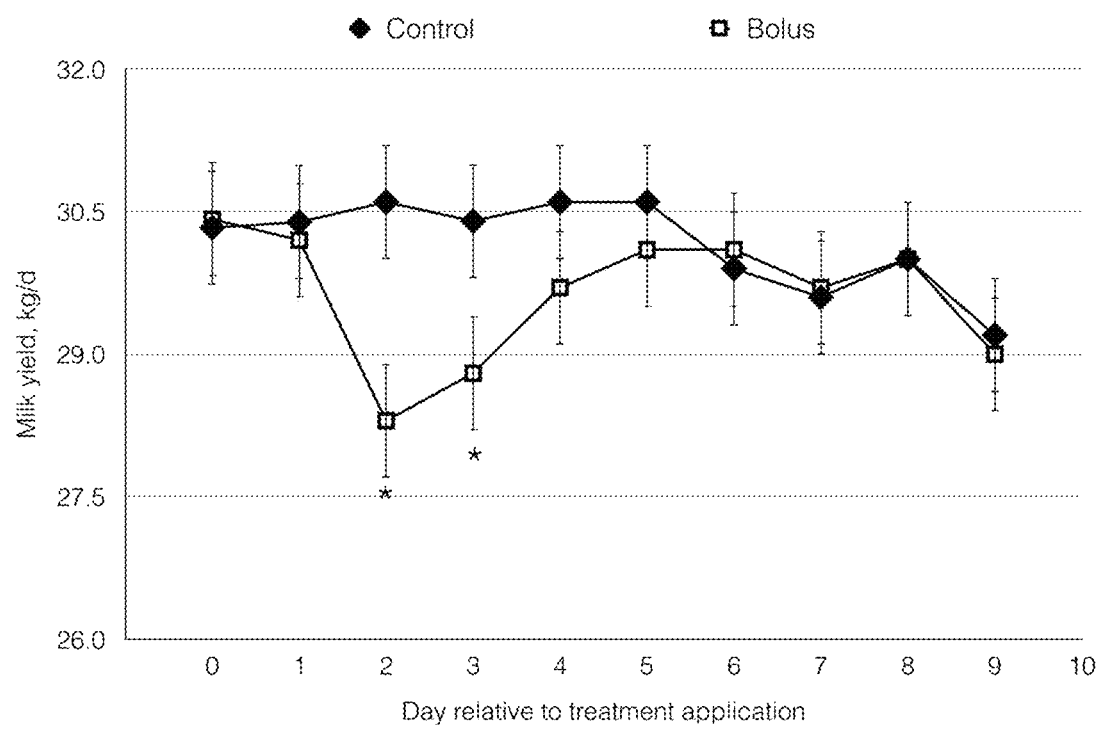
FIG. 4: shows milk yield as affected by bolus application [closed diamonds correspond to cows receiving no treatment (Control); open squares correspond to cows that received oral boluses (Bolus)]. Error bars depict SEM at each time point. Asterisk depicts difference (P<0.05) between Control and Bolus.

As observed in Example 1, milk production was reduced in >2 kg/d the second day after bolus application, and in this Example, milk production was also reduced on the third day after bolus application (FIG. 4). The reduction in milk yield might be, at least partly, explained by the decrease in DMI observed in Bolus cows.

Example 3

Animals and Experimental Design

A total of 152 Holstein cows from two commercial dairy farms in Girona, Spain, were enrolled in this study: 104 cows from SAT Sant Mer (Girona, Spain), and 48 cows from Mas to Duran (Girona, Spain). All cows were handled according to EEC Directive 86/609 covering the protection of animals used for experimental purposes. The study was also approved and supervised by the Animal Care Committee of IRTA. All enrolled were first blocked by parity and then randomly (using the random function from Excel, Microsoft Corp., Redmond, WA) assigned to 2 treatments. Experimental treatments consisted of a control group (Control) receiving no supplementation (n=76), and a treatment group (Bolus) receiving two oral boluses (n=76) supplying $NH_4Cl$ combined with $CaCl_2$ and $CaSO_4$ (Bovikalc Dry, Boehringer Ingelheim Vetmedica GmbH, Germany) administered 5 min apart about 12-8 h before the last milking prior to dry-off.

Cows were enrolled in the study 5 d before dry-off and monitored for 10 d following dry-off. The inclusion criteria for enrollment were a good general health based on physical inspection, ≥220 d of pregnancy, a daily milk yield >20 kg at drying-off, no signs of clinical mastitis, and four functional quarters. All cows from SAT Sant Mer farm were housed in a free-stall barn and had ad libitum access to lactation TMR ration and water until the moment of dry-off when they were moved to pens with sawdust bedding and changed to a dry-cow TMR ration offered also ad libitum. Cows from Mas Duran had the same feeding regime as at SAT Sant Mer, but they were housed in a compost-bedded pack barn with straw as bedding during both lactation and dry period. In both farms, lactating cows were milked in a 2×10 milking parlor 3 times a day at approximately 8-h intervals and individual daily milk yield was automatically recorded during each milking using electronic meters. At dry-off, cows from both farms were exposed to an abrupt cessation of milk and treated with an intra-mammary infusion of ceftiofur (Virbactan®, Virbac, Portugal). No teat sealant was applied to any cow at dry-off. During the course of the study, all animals and housing facilities were inspected twice daily, in the morning and in the afternoon, to ensure constant feed and water availability.

Measurements

All cows were equipped with an electronic data logger (Hobo Pendant G Acceleration Data Logger, Onset Computer Corporation, Pocasset, MA) for measuring cow activity from 5 d before to 10 d after dry-off at 1-min intervals. Each data logger was attached to one hind leg using vet wrap (Eurimex® flex, Divasa-Farmavic, SA, Barcelona, Spain) and oriented in a position such that the X axis of the HOBO loggers was pointing right, the Y axis was perpendicular to the ground, and the Z axis pointing away from the sagittal plane. The data collected by the HOBO loggers were downloaded using Onset HOBOware software (Onset Computer Corp., Bourne, MA, USA) and processed using a script written in the Python to calculate total lying time per day and cow as described by Yunta et al. (2012).

Blood samples were collected from twenty-five randomly-chosen cows per treatment group via the coccygeal vessels using 10-ml vacutainer tubes (BD Vacutainer Systems, Plymouth, UK) at 0, 8, 24 and 48 h after dry-off to determine pH, Ca, P, prolactin (PRL), non-esterified fatty acids (NEFA), and β-OH-butyrate (BHBA). Serum was then harvested and stored at −20° C. until further analysis.

Measurement of PRL concentration in serum was performed by ELISA (PRL/LTH) ELISA kit (Cusabio Biotech Co., Whuan, China). Blood Ca and P concentrations were determined by atomic absorption spectrophotometry. Blood BHBA concentration in serum was measured with a colorimetric method and the kit Autokit 3-HB (Wako Chemicals USA Inc., Richmond, VA). Concentration of NEFA in serum was measured using a colorimetric methods with the kit NEFA-HR(2) (Wako Chemicals USA Inc., Richmond, VA).

Following dry-off, presence or absence of ML was recorded twice daily on each cow at approximately 6-8 h intervals during three consecutive days. Milk leakage was defined as the observation of milk dripping or flowing from one or more teats. During the 3 d after dry-off, and on a daily basis, udder pressure was determined. For udder pressure, a digital algometer (Commander, JTech Medical Industries, Midvale, UT) that was modified by welding a 2-cm washer at 2 cm from the tip of the algometer was used as previously described by Bach et al. (2015). Briefly, the measure consisted of applying force to the caudo-ventral side of the rear left and right half udders with the tip of the algometer at 90° angle to the skin, and to stop applying force when the skin of the udder made contact with the washer. This procedure was performed for both the right and left rare quarters with three repetitions on each one until mean values with a coefficient of variation below 10% were obtained. Also, individual daily milk yield was measured for each cow using electronic meters until 60 DIM.

Statistical Analyses

Because treatment was applied at the animal level, the experimental unit was the animal. Measurements of udder pressure (conducted in the 2 rear quarters) were averaged within cow and sampling time before conducting statistical analysis.

All data from this experiment, except that pertaining to ML, were analyzed with a mixed-effects model with repeated measures using the PROC MIXED procedure of SAS. The fixed part of the model accounted for the effect of treatment, day, and their 2-way interaction, and the random part accounted for the effect of cow, block (parity), and herd. All models were subjected to an autoregressive variance covariance structure of first order as it yielded the lowest Bayesian information criterion values.

In addition, data pertaining to lying behavior collected for the 5 d preceding dry-off were averaged and used as a covariate to assess the potential impact of treatment on lying time during the 10 d following dry-off. The mixed-effects model used accounted for the fixed effect of treatment, day relative to dry-off, and their 2-way interaction, using lying time before dry-off as a covariate, and day as a repeated measure, plus the random effects of cow, block (parity), and herd.

Observations of ML were categorized as a binary response variable (1=presence of milk leakage; 0=absence of milk leakage) and processed with a mixed-effects logistic regression model using Stata (Version 14.2, StataCorp LLC, College Station, TX) that included the fixed effects of treatment, time, and the 2-way interaction, plus the random effect of cow and herd. Average milk yield 5 d before dry-off and days in pregnancy were 26.3±4.50 kg and 228.8±4.31 d in Control cows and 27.4±5.66 kg and 227.7±5.32 d in Bolus cows, respectively. Milk yield before dry-off and days in pregnancy did not differ between treatment groups.

Milk Production and Udder Health

No differences in milk production between treatments were observed during the days for which milk production was recorded (first 60 DIM), with an average milk yield of 41.5±1.09 kg/d for Bolus and 41.5±1.03 kg/d for Control cows. To our knowledge, no information is available about the potential effects of anionic salt supplementation at dry-off on milk production in the following lactation. The results herein indicate that anionic salt supplementation before dry-off had no detrimental effect on milk production in the following lactation.

One hundred and four cows (52 on each treatment group) were monitored for udder health during 200 d after calving. Out of these cows, 29 (27%) showed at least 1 case of mastitis.

The incidence of mastitis was not affected (P=0.79) by treatment, with cows on Control having 27.5% and cows on Bolus having a 26.4% incidence of mastitis. The lack of effect on the incidence of ML, which is a risk factor for mastitis, was probably, one of the reasons for the lack of differences in udder health after calving.

Udder Pressure

Figure 5:
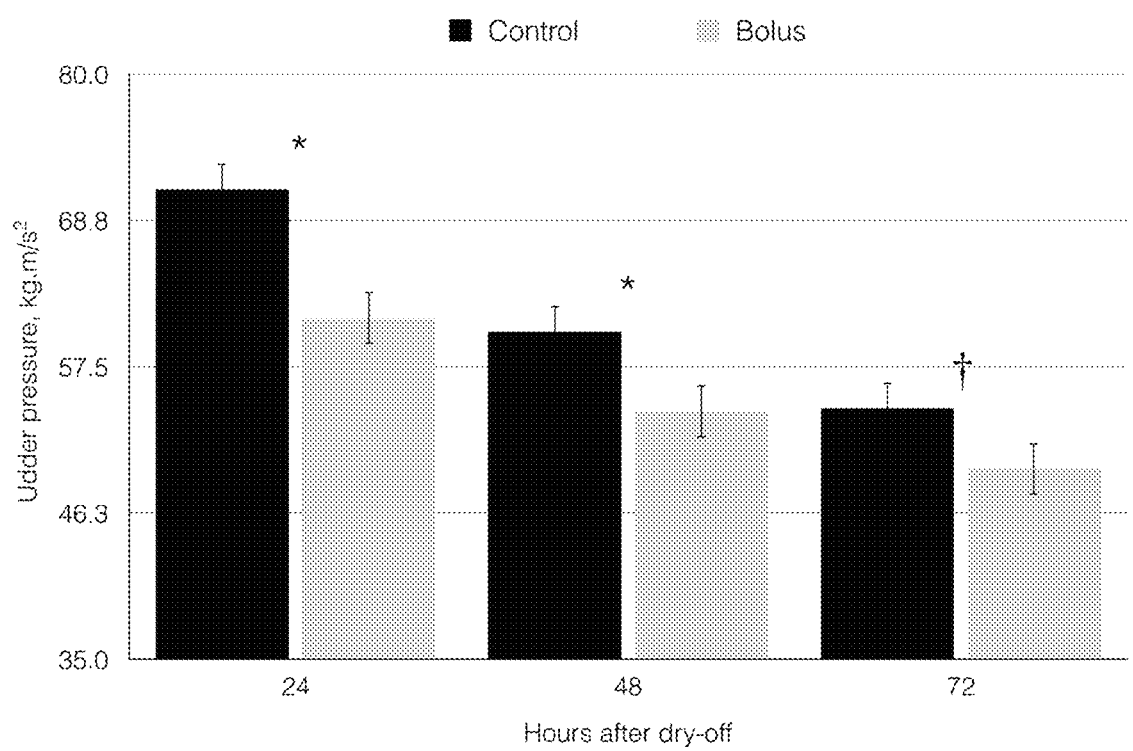
FIG. 5: shows udder pressure (kg·m/s$^2$) relative to dry-off as affected by bolus application [black bars correspond to cows receiving no treatment (Control); white bars correspond to cows that received oral boluses (Bolus)]. Error bars depict SEM at each time point. *depict difference (P<0.05), whereas † depicts a tendency (P<0.10) to differ between Control and Bolus.

Udder pressure decreased (P<0.05) with time after dry-off in both groups. Overall, average udder pressure after dry-off was lower (P<0.05) in Bolus (55.0±1.73 kg·m/s$^2$) than in Control (61.9±1.72 kg·m/s$^2$) cows. Differences in udder pressure were significant (P<0.05) at 24 and 48 h after dry-off, whereas at 72 h, Bolus cows tended (P<0.10) to have lower udder pressure than Control cows (FIG. 5). In line with Examples 1 and 2, these results support the hypothesis that application of acidogenic boluses before dry-off reduces milk production, and which, as shown in Example 3, it resulted in a decrease in milk accumulation in the udder as indicated by a lower udder pressure.

Lying Behavior

Figure 6:
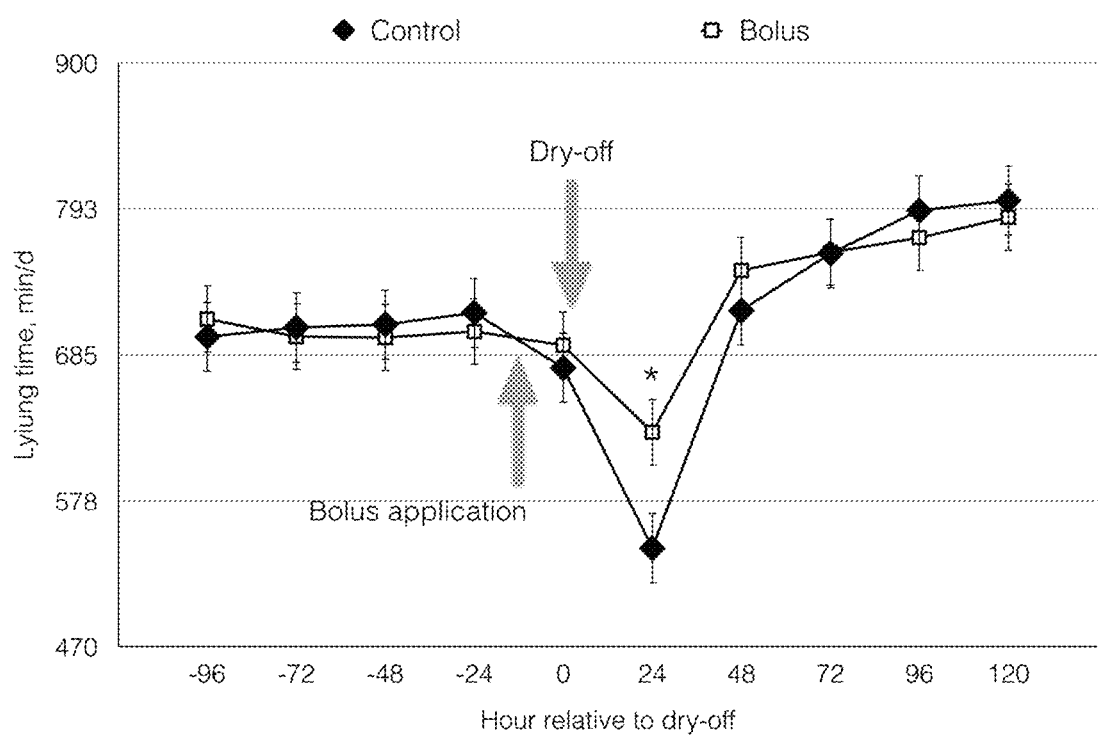
FIG. 6: shows time devoted to lie down (mind/d) as affected by bolus application [closed diamonds correspond to cows receiving no treatment (Control); open squares correspond to cows that received oral boluses (Bolus)]. Error bars depict SEM at each time point. Asterisk depicts difference (P<0.05).

Total daily lying time was not affected by treatment (P=0.98); however, an interaction (P<0.05) occurred between treatments and time relative to dry-off with cows in the Bolus group lying for an additional 85 min during the first 24-h after dry-off compared with Control cows (FIG. 6). This difference in daily lying time between Control and Bolus cows early after dry-off could be attributed to the greater udder pressure in Control than in Bolus.

Frequency of lying bouts was not affected by treatment (P=0.38); however, an interaction (P<0.05) between treatment and time was observed at day 2 after dry-off with Bolus cows on having lesser number of lying bouts (9.5±0.55 bouts/d) than in Control cows (10.8±0.54 bouts/d). The more frequent lying bouts in Control cows relative to Bolus cows could also be an indication of some discomfort due to udder pressure that may have forced Control cows to stand up. No difference (P=0.88) in the average duration of lying bouts was observed between Control and Bolus cows, but cows in the Bolus group had longer (P<0.05) lying bouts during the second day after dry-off (82.3±4.81 min/d) than Control cows (72.7±4.81 min/d).

REFERENCES (1) Bach A et al., J. Dairy Sci. 2015, 98:7097-7101
(2) Bach A et al., J. Dairy Sci. 2017, 101:1-10
(3) EP 0 943 246
(4) Goff J P, Vet. Clin. North Am. Food Anim. Pract. 1999, 15:619-639
(5) NRC 2001, Nutrient Requirements of Dairy Cattle. 7th ed. Natl. Acad. Press, Washington, DC
(6) Oetzel G R and Miller B E, Journal of Dairy Science 2012, 95(12): 7051-7065
(7) Rérat M and Schlegel P, Journal of Animal Physiology and Animal Nutrition 2013, 98(3): 458-466
(8) Stokes S R, http://oaktrust.library.tamu.edu/bitstream/handle/1969.1/86766/pdf_1016.pdf?sequence=1
(9) US 2002/0150633
(10) U.S. Pat. No. 5,360,823
(11) Yunta C I et al., J. Dairy Sci. 2012, 95:6546-6549

The invention claimed is:

1. A method of improving and/or facilitating drying-off of a cow comprising administering to the cow an oral acidogenic bolus, wherein the oral acidogenic bolus comprises a plurality of acidifying agents, wherein the acidifying agents comprise ammonium chloride, calcium chloride and calcium sulfate, and wherein the acidogenic bolus is administered before drying-off of the cow.

2. The method of claim 1, wherein the cow is pregnant.

3. The method of claim 1, wherein the acidogenic bolus is administered at least from 1 to 4 times before drying-off.

4. The method of claim 1, wherein the acidogenic bolus is administered on the last milking day.

5. The method of claim 1, wherein the acidogenic bolus is administered twice on a last milking day and/or before drying-off.

6. The method of claim 1, wherein the administration of the oral acidogenic bolus is from 8 to 12 hours before the last milking day.

7. The method of claim 1, wherein the cow is a Holstein cow.

8. The method of claim 1, wherein the administering results in reduction of milk production in the cow, for at least 48 hours following the bolus administration.

9. The method of claim 1, wherein the administering results in one or more further effects selected from the group consisting of:
   (a) decrease of milk accumulation in the udder, and thereby reduced udder pressure, during one or more days after drying-off when the bolus administration occurrs 8 hours to 12 hours before drying-off;
   (b) increase of daily lying time on the day after drying-off;
   (c) induction of a mild and temporary metabolic acidosis at after drying-off;
   (d) reduction of dry matter intake (DMI) during one or more days after drying-off; and
   (e) reduction of urine pH following the bolus administration.

10. An acidogenic bolus comprising ammonium chloride, calcium chloride and calcium sulfate, wherein the bolus includes calcium chloride in an amount from 40% (w/w) to 60% (w/w).

11. The acidogenic bolus of claim 10, wherein the bolus includes calcium sulfate in an amount from 15% (w/w) to 25% (w/w).

12. The acidogenic bolus of claim 11, wherein the bolus includes ammonium chloride in an amount from 5% (w/w) to 15% (w/w).

13. The acidogenic bolus of claim 10, wherein the bolus includes ammonium chloride in an amount from 5% (w/w) to 15% (w/w).

* * * * *